US012213829B2

(12) United States Patent
Rupcich et al.

(10) Patent No.: US 12,213,829 B2
(45) Date of Patent: Feb. 4, 2025

(54) METHOD AND SYSTEM FOR SELECTION OF REFERENCE SCOUT IMAGES FOR X-RAY SOURCE CURRENT MODULATION

(71) Applicant: GE Precision Healthcare LLC, Wauwatosa, WI (US)

(72) Inventors: Franco Rupcich, Wauwatosa, WI (US); Chelsey Amanda Lewis, Waukesha, WI (US); Bradley Jay Gabrielse, Brookfield, WI (US); Jacquelyn Lee Gerhardson, Milwaukee, WI (US)

(73) Assignee: GE PRECISION HEALTHCARE LLC, Wauwatosa, MN (US)

( * ) Notice: Subject to any disclaimer, the term of this patent is extended or adjusted under 35 U.S.C. 154(b) by 204 days.

(21) Appl. No.: 18/160,392

(22) Filed: Jan. 27, 2023

(65) Prior Publication Data
US 2024/0252135 A1 Aug. 1, 2024

(51) Int. Cl.
A61B 6/00 (2024.01)
A61B 6/03 (2006.01)
A61B 6/40 (2024.01)
A61B 6/46 (2024.01)

(52) U.S. Cl.
CPC .............. A61B 6/542 (2013.01); A61B 6/032 (2013.01); A61B 6/405 (2013.01); A61B 6/4435 (2013.01); A61B 6/463 (2013.01); A61B 6/465 (2013.01); A61B 6/467 (2013.01); A61B 6/488 (2013.01)

(58) Field of Classification Search
CPC ......... A61B 6/542; A61B 6/032; A61B 6/405; A61B 6/4435; A61B 6/463; A61B 6/465; A61B 6/467; A61B 6/488; A61B 6/469; A61B 6/545
See application file for complete search history.

(56) References Cited

U.S. PATENT DOCUMENTS

2012/0150505 A1* 6/2012 Couch .................. G01T 1/02
703/2

OTHER PUBLICATIONS

Ryu et al., "Effect of arm position, presence of medical devices, and off-centering during acquisition of scout image on automatic tubevoltage selection and current modulation in pediatric chest CT", PLOS ONE, 12 pages. (Year: 2018).*

* cited by examiner

Primary Examiner — Kiho Kim
(74) Attorney, Agent, or Firm — Daugherty & Del Zoppo, Co. LPA

(57) ABSTRACT

A system(s), a computer-implemented method(s) and/or computer executable instructions encoded on a computer readable medium(s) obtains, for groups of a scan series for a subject, scout images for the subject that were acquired prior to planning the scan series and that include images of arms of the subject in different positions relative to the subject, designates, for each group of the groups, a scout image of the scout images with a position of the arms of the subject that corresponds to a position of the arms of the subject in the group as the reference image for X-ray source current modulation for the group, and utilizes the designated scout images for X-ray source current modulation for the series.

20 Claims, 8 Drawing Sheets

METHOD AND SYSTEM FOR SELECTION OF REFERENCE SCOUT IMAGES FOR X-RAY SOURCE CURRENT MODULATION

CROSS-REFERENCE TO RELATED APPLICATIONS

The present application is related to co-pending U.S. patent application Ser. No. 18/160,430 filed on Jan. 27, 2023 and entitled "METHOD AND SYSTEM FOR SUBJECT POSITION INSTRUCTIONS DURING AN IMAGING EXAMINATION" and co-pending U.S. patent application Ser. No. 18/160,461 filed on Jan. 27, 2023 and entitled "METHOD AND SYSTEM FOR CREATING A REFERENCE SCOUT IMAGE FOR X-RAY SOURCE CURRENT MODULATION."

FIELD

The following generally relates to computed tomography (CT) and more particularly to a method and system for selection of scout reference images for X-ray source current modulation.

BACKGROUND

Computed tomography (CT) scanners generate volumetric image data with information about the interior of a subject (e.g., tissue, organs, etc.) or an object. Before a volumetric scan, a scout (also referred to as a scanogram, a topogram, a surview, a localizer, a pilot, etc.) image is acquired. Generally, a scout image is a two-dimensional (2-D) projection image along a portion of a longitudinal axis of a subject or object (similar to an X-ray radiograph) and is used during scan planning to identify start and end scan positions for the scan and as a reference image for X-ray tube current modulation. With X-ray tube current modulation, the X-ray tube current is modulated based on a thickness and radiation attenuation of tissues, e.g., increasing the X-ray tube current for thicker and bonier regions such as the chest and decreasing the X-ray tube current for thinner and less boney region such as the neck. In general, the last scout image acquired for a subject is automatically designated as the "reference" image for X-ray tube current modulation for scanning the subject.

Some volumetric scans include a series of scan groups such as a first group followed by at least a second group. An example of such a series is a chest/abdomen/pelvis scan followed by a head/neck scan. With such a series, the subject is instructed to raise their arms above their head for the first group. Once their arms are correctly positioned, the chest/abdomen/pelvis scan is performed. After the chest/abdomen/pelvis scan, the subject is instructed to lower their arms to their side for the second group. Once their arms are correctly positioned, the head/neck scan is performed. In this instance, the reference image for X-ray tube current modulation reflects the subject with their arms above their head, and the arm position of the subject in the reference image will not match the arm position of the subject for the head/neck scan of the series. As a consequence, there may be sub-optimal radiation dose and/or image quality for the second group in the series.

For example, the subject may receive a higher radiation dose than prescribed for a given image quality for the second group at least because the software determined the X-ray tube current modulation profile based on the subject with their arms over their head and thus considers their arms even though the scan is performed with their arms at their side. With some series, there is not enough time between the groups to acquire another scout to match the arm position in the subsequent group. An example of such a series is a single bolus chest/abdomen/pelvis scan followed by a head/neck contrast medium enhanced scan, where the scan plan is set up to capture peak uptake of the contrast agent. With such a series, although there is enough time between the groups for the subject to reposition their arms (from above their head to their side), peak uptake of the contrast agent may be missed in the latter group of the series were a scout scan performed between the groups of the series.

In view of at least the foregoing, there is an unresolved need for an improved approach(es) for modulating X-ray source current during imaging based on a scout image for certain scan series.

SUMMARY

Aspects described herein address the above-referenced problems and others. This summary introduces concepts that are described in more detail in the detailed description. It should not be used to identify essential features of the claimed subject matter, nor to limit the scope of the claimed subject matter.

In one aspect, a computed tomography imaging system includes a rotating frame configured to rotate about a rotational axis, an X-ray source disposed on the rotating frame and configured to emit X-ray radiation that traverses an examination region, an X-ray controller configured to control the X-ray source, a subject/object support configured to support a subject or object in the examination region, and a console with a computer readable medium configured to store instructions and a processor configured to execute the instructions. The instructions cause the processor to obtain a first scout image with arms of a subject up above shoulders of the subject, obtain a second scout image with arms of the subject down by sides of the subject, designate the first scout image as a reference image for X-ray source current modulation for a first group of a scan series where the arms of the subject are up above the shoulders of the subject, designate the second scout image as a reference image for X-ray source current modulation for a second group of the scan series where the arms of the subject are down by the sides of the subject, and command the X-ray controller to utilize the first scout image as the reference image for X-ray source current modulation for the first group of the scan series and the second scout image as the reference image for X-ray source current modulation for the second group of the scan series.

In another aspect, a computer-implemented method includes obtaining a first scout image for a first group of a scan series, wherein the first scout image includes arms of a subject up above shoulders of the subject. The computer-implemented method further includes obtaining a second scout image for a second group of the scan series, wherein the second scout image includes arms down by sides of the subject. The first scout image and the second scout image are acquired prior to planning the scan series, the first group includes the arms of the subject up above the shoulders of the subject, and the second group includes the arms of the subject down by the sides of the subject. The computer-implemented method further includes designating the first scout image as a reference image for X-ray source current modulation for the first group. The method further includes designating the second scout image as a reference image for X-ray source current modulation for the second group.

In another aspect, a computer readable medium is encoded with computer executable instructions. The computer executable instructions, when executed by a processor, cause the processor to obtain a first scout image for a first group of a scan series, wherein the first scout image includes arms of a subject up above shoulders of the subject. The computer executable instructions, when executed by the processor, further cause the processor to obtain one or more additional scout image for one or more additional group of the scan series, wherein the one or more additional scout image includes arms down by sides of the subject. The first scout image and the one or more additional scout image are acquired prior to planning the scan series, the first group includes the arms of the subject up above the shoulders of the subject, and the one or more additional group includes the arms of the subject down by the sides of the subject. The computer executable instructions, when executed by the processor, further cause the processor to designate the first scout image as a reference image for X-ray source current modulation for the first group. The computer executable instructions, when executed by the processor, further cause the processor to designate the one or more additional scout image as a reference image for X-ray source current modulation for the one or more additional group.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

Embodiments of the present disclosure will now be described, by way of example, with reference to the Figures, in which a system(s), a computer-implemented method(s) and/or computer executable instructions encoded on a computer readable medium(s), in one instance(s) obtains, for groups of a scan series for a subject, scout images for the subject that were acquired prior to planning the scan series and that include images of arms of the subject in different positions relative to the subject, designates, for each group of the groups, a scout image of the scout images with a position of the arms of the subject that corresponds to a position of the arms of the subject in the group as the reference image for X-ray source current modulation for the group, and utilizes the designated scout images for X-ray source current modulation for the series, in another instance(s) receives a current position of arms of a subject for a group of a scan series, automatically identifies a scout image from a set of scout images with images of the subject with arms in different positions relative to the subject in which arms of the subject are at a position relative to the subject that corresponds to the current position of the arms of the subject, and utilizes the identified scout image for X-ray source current modulation for the group, and/or in another instance(s) obtains, for a scan series for a subject that includes arms of the subject at different positions relative to the subject, a scout image for the subject, removing the arms of the subject from the scout image, designating the scout image with the arms of the subject removed as a reference image for X-ray source current modulation for the scan series, and utilizes the designated scout image for X-ray source current modulation for the scan series.

Figure 1:
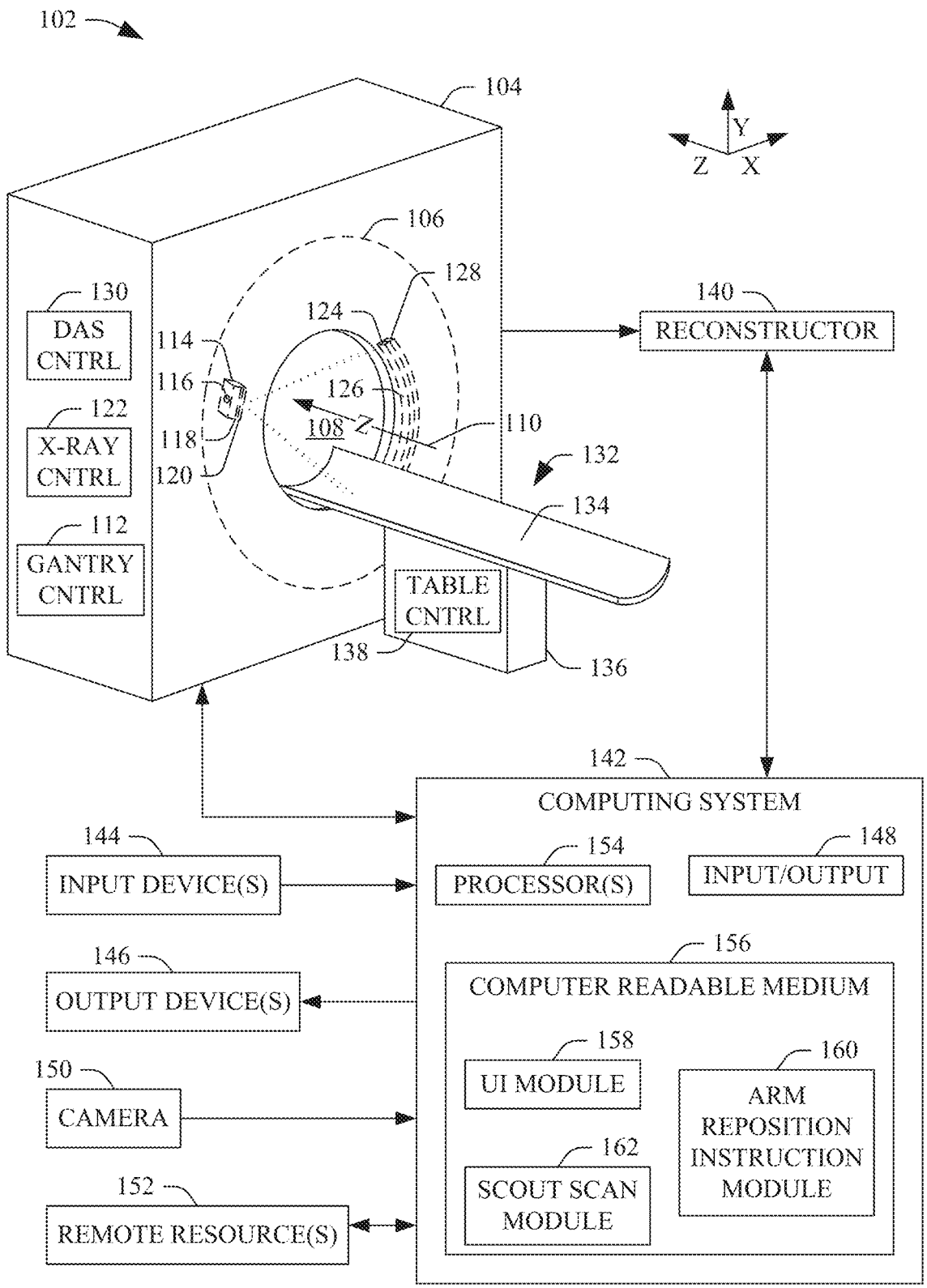
FIG. 1 schematically illustrates a non-limiting example of an imaging system with a scout scan module, in accordance with an embodiment(s) herein.

FIG. 1 schematically illustrates a non-limiting example of an imaging system 102 such as a computed tomography (CT) imaging system. The imaging system 102 includes a generally stationary (i.e. non-rotating) gantry 104 and a rotating frame 106. The rotating frame 106 is rotatably supported by the stationary gantry 104, e.g., via a bearing or the like, and is configured to rotate around an examination region 108 about a rotational or z-axis 110. In some instances, the stationary gantry 104 can be configured to tilt through the z-axis 110. A gantry controller (GANTRY CNTRL) 112 is configured to control rotation (and tilt, if available) of the rotating frame 106, including no rotation.

An X-ray source assembly 114 is supported by the rotating frame 106 and rotates in coordination with the rotating frame 106. The X-ray source assembly 114 includes an X-ray source 116 such as an X-ray tube. The X-ray source 116 is configured to emit X-ray radiation having an energy in the diagnostic range. The X-ray assembly 114 may further include or is coupled to a filter 118 that characterizes a radiation dose profile and/or a collimator 120 that shapes the X-ray radiation to form a generally fan, wedge, cone, etc. shaped beam that traverses the examination region 108. An X-ray controller (X-RAY CNTRL) 122 is configured to control components of the X-ray assembly 114 such as radiation emission of the X-ray source 116, the collimator 120, etc.

A radiation sensitive detector 124 includes a one- or two-dimensional (1-D or 2-D) array of rows of radiation sensitive detector elements 126 and is supported by the rotating frame 106 along an arc opposite the X-ray source 116, across the examination region 108. Each radiation sensitive detector element of the array of rows of radiation sensitive detector elements 126 is in electrical communication with data acquisition electronics 128. A data acquisition electronics controller (DAS CNTRL) 130 controls the data acquisition electronics 128.

A subject/object support 132 includes a tabletop 134 moveably coupled to a frame/base 136. In one instance, the tabletop 134 is slidably coupled to the frame/base 136 via a bearing or the like, and a drive system (not visible) including a controller, a motor, a lead screw, and a nut (or other drive system) translates the tabletop 134 along the frame/base 136 into and out of the examination region 108. The tabletop 134 is configured to support an object or subject in the examination region 108 for loading, scanning, and/or unloading the subject or object. A table controller (TABLE CNTRL) 138 controls the drive system.

For a helical scan, the rotating frame 106 rotates in coordination with moving the tabletop 134 along the Z-axis 110, and active detector elements 126 of the radiation sensitive detector 124 detect radiation over consecutive arc segments (integration periods) each revolution and generate respective signals. For each arc segment, the data acquisition electronics 128 processes each signal and generates projection data. For a scout scan, the rotating frame 106 remains at a static angular position while the tabletop 134 along the Z-axis 110 and active detector elements 126 of the radiation sensitive detector 124 detect radiation.

A reconstructor 140 reconstructs the projection data and generates volumetric image data for a helical scan, individual axial images for an axial step and shoot scan (which can be used in combination to generate volumetric image data), and/or a scout scan image for a scout scan. Examples of suitable reconstruction algorithms include filtered back projection (FBP), advanced statistical iterative reconstruction (ASIR), conjugate gradient (CG), maximum likelihood expectation maximization (MLEM), model-based iterative reconstruction (MBIR), and/or other reconstruction algorithm.

A computing system 142 serves as an operator console for the system 102. An input device(s) 144 such as a keyboard, mouse, touchscreen, microphone, etc. and an output device(s) 146 includes a human readable device such as a display monitor or the like. The computing system 142 includes input/output (I/O) 148. A camera 150 is in electrical communication with the computing system 142 via the I/O 148. The camera 150 can be attached to the system 102, a wall or ceiling in the examination room, a support device, etc., and a real-time signal can be provided thereby to the computing system 142.

A remote resource(s) 152 is also in electrical communication with the computing system 142 via the I/O 148. The remote resource(s) 152 may include cloud processing resources, a server, a workstation, a Radiology Information System (RIS), a Hospital Information System (HIS), an electronic medical record (EMR), a Picture Archiving and Communications System (PACS), etc. In another instance, the remote resource(s) 152 also include one or more other CT scanners.

The computing system 142 further includes a processor(s) 154 such as a microprocessor, a central processing unit (CPU), etc., and computer readable storage medium 156, which includes non-transitory medium and excludes transitory medium (signals, carrier waves, and the like). The computer readable storage medium 156 is embedded or encoded with computer executable instructions (computer code), and the processor(s) 154 is configured to execute at least one of the computer executable instructions. A user interface (UI) module 158 provides a user interface with which a user interacts with the system 102, e.g., for acquiring a scout image, setting up a series of multiple groups of scans, identifying scout image(s) to use for X-ray source current modulation for groups of the series in some instances, starting a series, etc. An arm reposition instruction module 160 facilitates providing certain instructions for when and where a subject should reposition their arms during groups in a series.

The scout scan module 162 is configured to facilitate designating a scout image(s) to groups of a series. As discussed herein, a non-limiting example of such a series includes a first group for a first sub-portion of a subject, e.g., above (or below) the shoulders, followed by a second group for a second different sub-portion of the subject, e.g., below (or above) the shoulders, where a position of arms of the subject for the first group is different than the position of the arms for the second group, the scout image is acquired before the series, and there is not enough time between groups to perform a second scout scan to acquire an X-ray source current modulation reference image where the arm position of the subject matches the arm position of the subject for the second group.

As described in greater detail below, in one instance the scout scan module 162 either creates a single X-ray source current modulation reference image that is suitable for all groups in the series (and can also be used for scan planning) in that there is no arm position mismatch between the reference image for any group, and, in another instance designates different scout images, all acquired prior to planning the series, as reference images to different groups so that each group has an X-ray source current modulation reference image with an arm position that matches the arm position for the group. In one instance, this mitigates utilizing a reference image for groups in a series that may result in sub-optimal subject radiation dose and/or image quality for at least one of the groups of the series.

Figure 2:
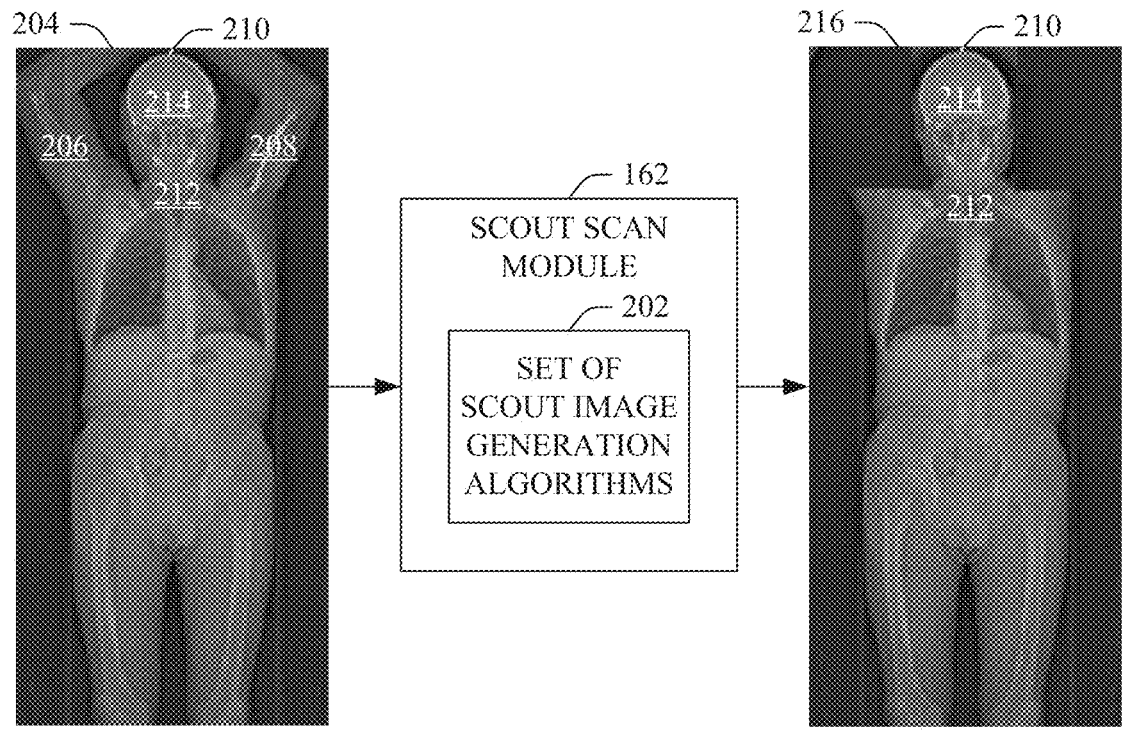
FIG. 2 schematically illustrates a non-limiting example of the scout scan module, in accordance with an embodiment(s) herein.

FIG. 2 schematically illustrates a non-limiting example of the scout scan module 162. The scout scan module 162 includes a set of (i.e. one or more) scout image generation algorithms 202. The scout scan module 162 receives a last acquired scout image 204 as input. In the last scout image 204, arms 206 and 208 of a subject 210 are positioned above a shoulder region 212 and by a head 214 of the subject 210 (arms up). With another suitable input scout scan image 204, the arms of the subject are positioned at a side of the torso of the subject (arms down). An algorithm of the set of scout image generation algorithms 202 generates a new scout scan image 216 that does not include the arms 206 and 208 based on the input scout scan image 216.

In one instance, the algorithm of the set of scout image generation algorithms 202 segments a region of the input scout scan image 204 that includes the arms 206 and 208 of the subject 210 and modifies values of the pixels therein, e.g., setting values of the pixels of the segmented region to zero. In one instance, the segmentation process includes comparing values of pixels with a threshold pixel value such as a pixel value corresponding to around an intensity of air and less than an intensity of tissue. In this manner, the algorithm distinguishes the arms 206 and 208 from a head 214 of the subject based on at least non-tissue between the arms 206 and 208 and the head 214 in the scout image 216.

The new scout scan image 216 is utilized as the last acquired scout scan image in place of the scout scan image 204. With the arms 206 and 208 excluded, the new scout scan image 216 can be utilized as the reference image for all groups of the series without a mismatch with the position of the arms, regardless of whether the arms of the subject are up or down during scanning. With this instance, a scout scan with either arms up or arms down is acquired before planning and performing the series. The subject still moves their arms between groups of the series, e.g., from arms up to arms down, but the new scout scan image 216 (with no arms) is utilized for X-ray source current modulation for both groups of the series.

In another instance, an algorithm of the set of scout image generation algorithms 202 includes an anatomical atlas or model. In this instance, anatomical landmarks of the anatomical atlas or model are used to identify the arms 206 and 208 in the input scout image 204 and then the arms 206 and 208 removed, e.g., by setting values of pixels corresponding to the arms 206 and 208 to zero and/or otherwise. Likewise, a scout scan with either arms up or arms down is acquired before planning and performing the series, and the subject still moves their arms between group of the series, e.g., from arms up to arms down, but the new scout scan image 216 (with no arms) is utilized for X-ray source current modulation for both groups of the series.

Figure 3:
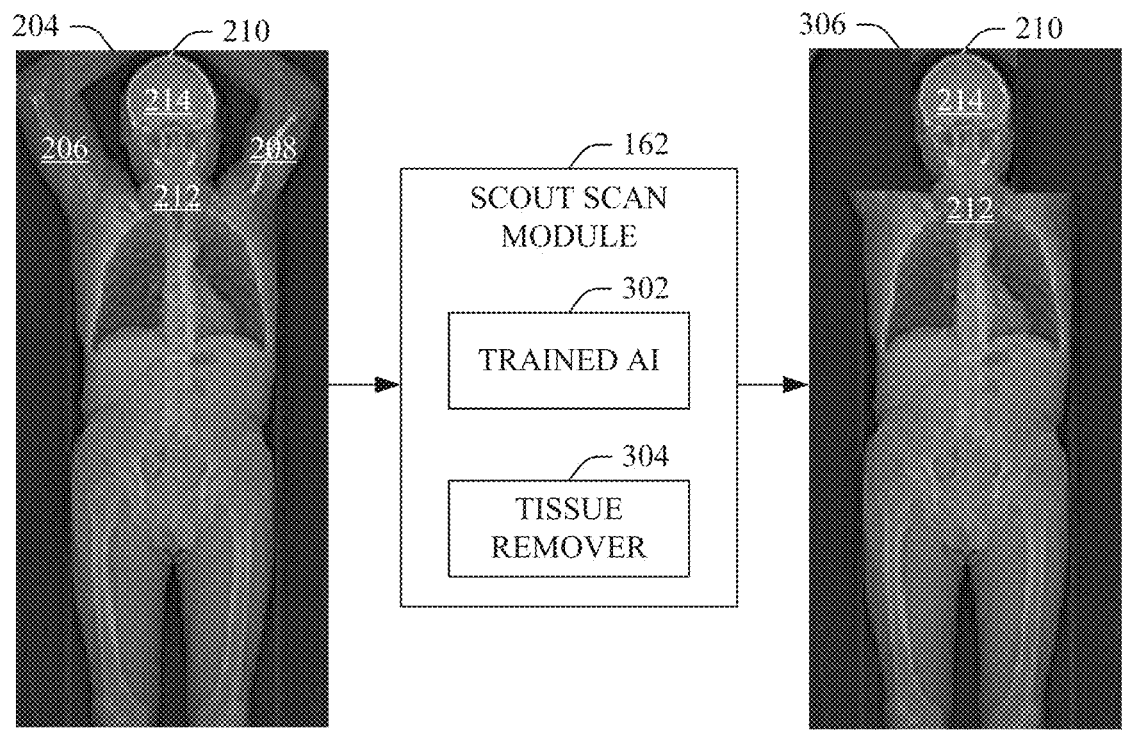
FIG. 3 schematically illustrates another non-limiting example of the scout scan module, in accordance with an embodiment(s) herein.

FIG. 3 schematically illustrates another non-limiting example of the scout scan module 162. The scout scan module 162 includes trained artificial intelligence (trained AI) 302 and a tissue remover 304. The scout scan module 162 receives a last acquired scout image 204 as input. In the last scout image 204, arms 206 and 208 of a subject 210 are positioned arms up. With another suitable input scout scan image, the arms of the subject are positioned arms down. The trained AI 302 and tissue remover 304 generate a new scout scan image 306 that does not include the arms 206 and 208 based on the input scout scan image 204.

For training the artificial intelligence, in one instance, a training set of images includes scout images acquired with arms up to learn images with the arms of the subject up above the shoulders. Additionally, or alternatively, a training set of images includes scout images acquired with arms up to learn images with no arms down by a side of the subject. Additionally, or alternatively, a training set of images includes scout images acquired with arms down to learn images with arms down by a side of the subject. Additionally, or alternatively, a training set of images includes scout images acquired with arms down to learn images with no arms of the subject up above the shoulders. Once trained, the AI 302 evaluates the input scout image 204 and identifies the arms 206 and 208 therein, and the tissue remover 304 modifies the input scout scan image 204 to remove the arms 206 and 208, e.g., by setting values of pixels of the identified arms 206 and 208 to zero, and/or otherwise.

The new scout scan image 306 is utilized as the last acquired scout scan image in place of the scout scan image 204. With the arms 206 and 208 excluded, the new scout scan image 306 can be utilized as the reference image for all groups of the series without a mismatch with the position of the arms, regardless of whether the arms of the subject are up or down during scanning. With this instance, a scout scan with either arms up or arms down is acquired before planning and performing the series. The subject still moves their arms between group of the series, e.g., from arms up to arms down, but the new scout scan image 306 (with no arms) is utilized for X-ray source current modulation for both groups of the series.

It is to be appreciated that with FIGS. 2 and 3 the arm removal does not have to be exact in the new scout image. That is, in one instance, the algorithm and/or trained AI may not identify every single pixel that includes a contribution from the arms. In one instance, if the user and/or an algorithm decides that there is too much arm remaining in the new scout image, e.g., based on percentage of total arms, the region of the arms, etc., the new scout image can be processed using the algorithm and/or trained AI. In another instance, the original scout image can be processed again. In another instance, the user can manually remove such pixels by identifying them to the system and changing the pixel values.

Figure 4:
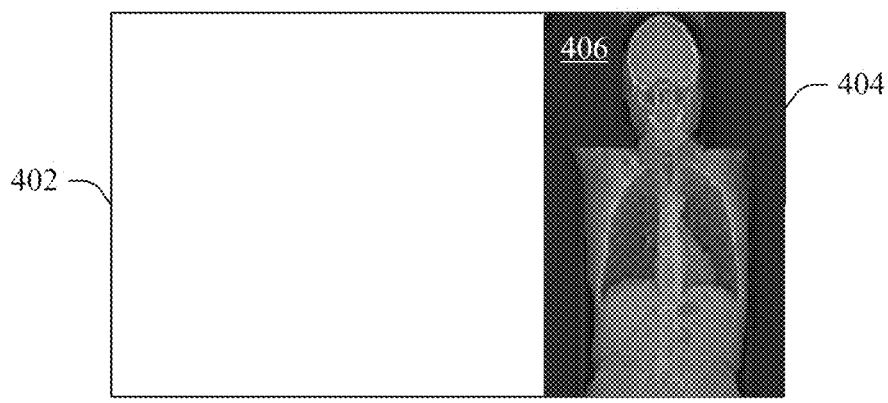
FIG. 4 schematically illustrates a non-limiting example of a scan planning user interface with a scout image, in accordance with an embodiment(s) herein.
Figure 5:
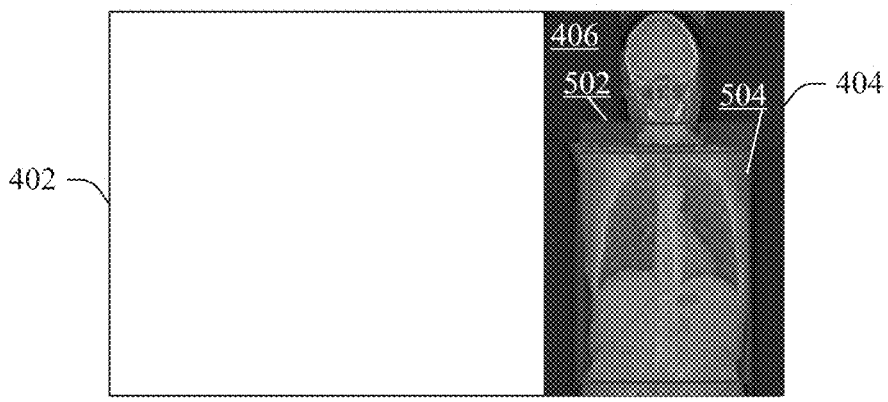
FIG. 5 schematically illustrates the scan planning user interface with scan range areas superimposed over the scout image, by the scout scan module based on the scout image generated from a scout scan, in accordance with an embodiment(s) herein.

FIG. 4 schematically illustrates a non-limiting example of a scan planning user interface 402. The user interface 402 includes at least one planning viewport 404. The location, size and/or shape of at least one planning viewport 404 is provided for explanatory purposes and is not limiting. A scout image 406 with no arms (e.g., one of the new scout scan images 216 or 306) is displayed in the at least one planning viewport 404. FIG. 5 schematically illustrates a first planned diagnostic field of view (DFOV) 502 for a first group of the series and a second planned DFOV 504 for a second group of the series.

In another instance, the input scout scan image 204 is displayed in the at least one planning viewport 404. In another instance, the scout image displayed in the at least one planning viewport 404 is based on a default configuration, a user preference, a healthcare facility preference, etc. In another instance, a user selects which of the scout scan images 204, 216 or 306 is displayed in the at least one planning viewport 404. In another instance, a user can toggle between displaying the new scout scan images 204, 216 and 306 in the at least one planning viewport 404.

In another instance, UI 402 includes multiple planning viewports. In this instance, multiple scout images can be concurrently displayed. By way of example, in some instances, scout scans are performed from different angular positions (e.g., posterior-to-anterior (PA) or AP, and lateral. In such an instance, the PA or AP and the lateral scout images can be concurrently displayed in different planning viewports. This includes displaying the scout image 204, 216 or 306 in one viewport and the lateral scout image in another viewport.

Figure 6:
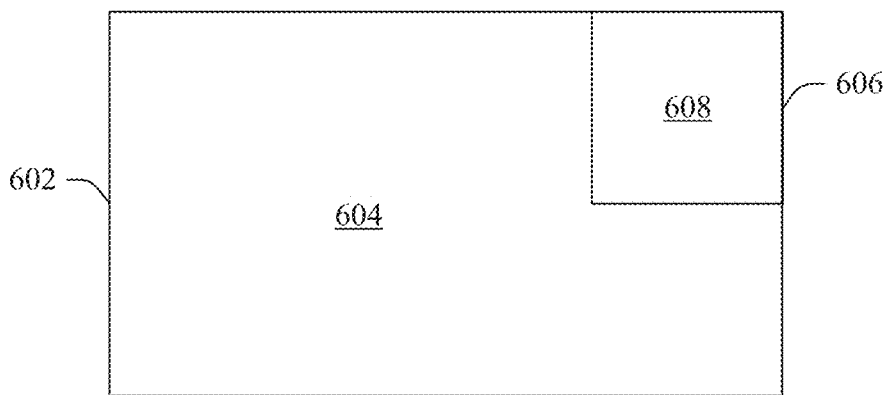
FIG. 6 schematically illustrates a non-limiting example of a scanning user interface with a scout image, in accordance with an embodiment(s) herein.

FIG. 6 schematically illustrates a non-limiting example of a scanning user interface 602. The user interface 602 includes at least one viewport in a region 604 for displaying one or more images as images are being reconstructed and at least one planning viewport 606 for displaying a reference image 608 showing a location of the currently displayed reconstructed image. The reference image 608 can be the scout image 204, 216 or 306. The displayed reference image can be based on a default configuration, a user preference, a healthcare facility preference, etc.

Figure 7:
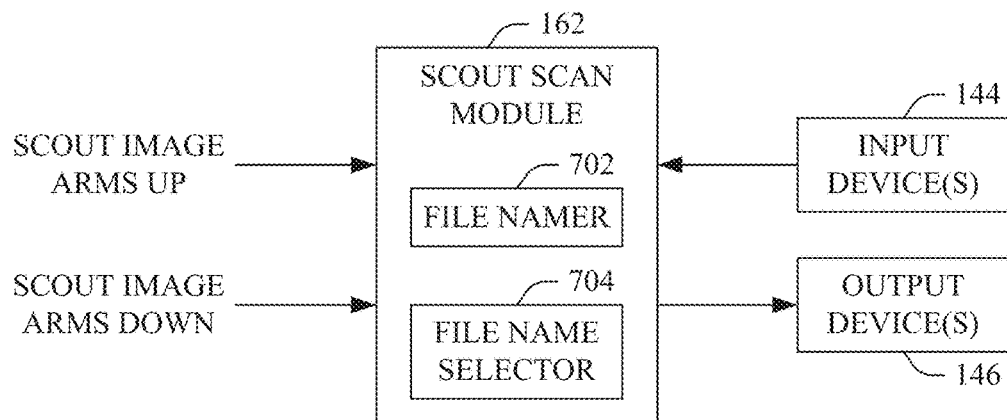
FIG. 7 schematically illustrates another non-limiting example of a scout scan module, in accordance with an embodiment(s) herein.

FIG. 7 schematically illustrates another non-limiting example of the scout scan module 162. The scout scan module 162 includes a file namer 702 and a file name selector 704. The scout scan module 162 receives two scout images, one with the arms of the subject up and one with the arms of the subject down, both acquired prior to performing a series that includes a first group with the arms of the subject up above the shoulders and a second group with the arms of the subject down at a side of the subject. The file namer 702 is configured to name a scout image based on a user input, and the file name selector 704 is configured to retrieve a saved scout image based on a user input identifying the name of the scout image.

By way of non-limiting example, after a scout image is acquired, the scout scan module 162 prompts a user for a name for the file, e.g., via a display monitor of the output device(s) 146. The scout scan module 162 receives a user input, e.g., via an input device of the input device(s) 144, and the scout image file is saved according to the input name. In one instance, the user inputs a user-created name. Generally, the name should identify whether the arms are up or down so that each can be readily identified later by name. In another instance, the user is given a choice of names, e.g., scout image arms up and scout image arms down, and the user selects one of the two names.

After the second scout image is acquired before the series, the scout scan module 162 again prompts a user for a name for the file, e.g., via a display monitor of the output device(s) 146, and receives a user input, e.g., via an input device of the input device(s) 144, and the scout image file is saved according to the input name. The user similarly names the file, e.g., either with a user-created name or a predetermined name. In another instance, the second scout image is automatically named with the non-selected name of the displayed name options. The user can change the name of either or both of the scout images.

Figure 8:
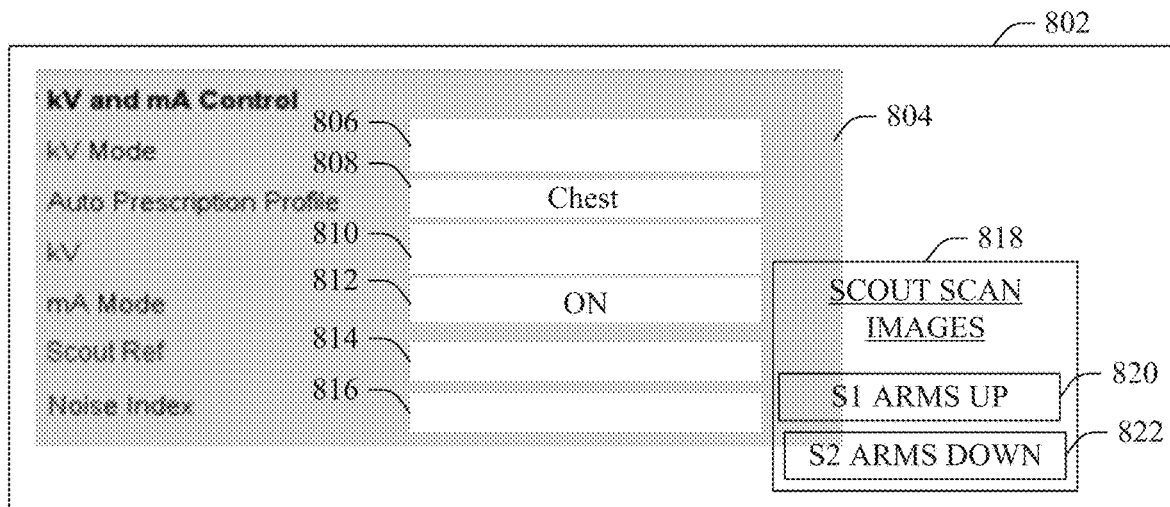
FIG. 8 schematically illustrates a non-limiting example of a protocol management window for a first group of a series with an unpopulated scout reference image field, in accordance with an embodiment(s) herein.
Figure 9:
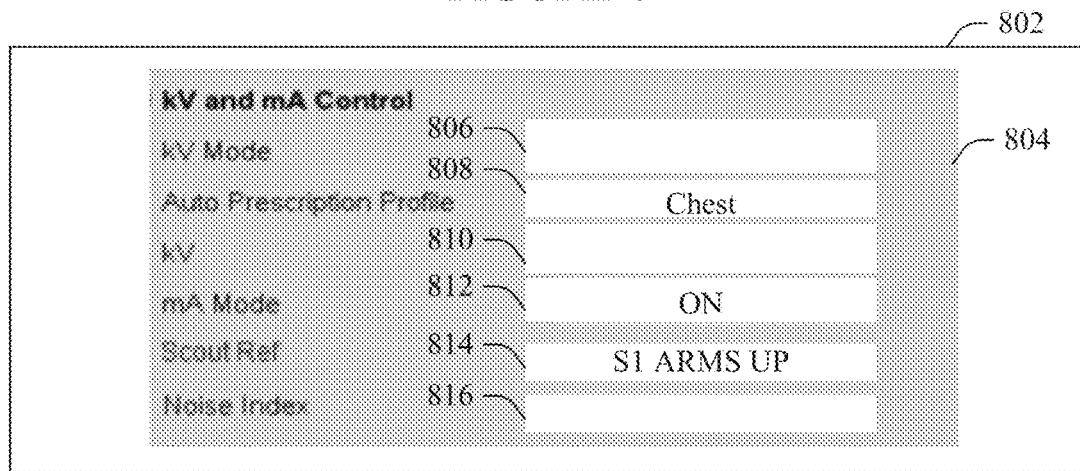
FIG. 9 schematically illustrates the protocol management window for the first group of the series with the scout reference image field populated, in accordance with an embodiment(s) herein.
Figure 10:
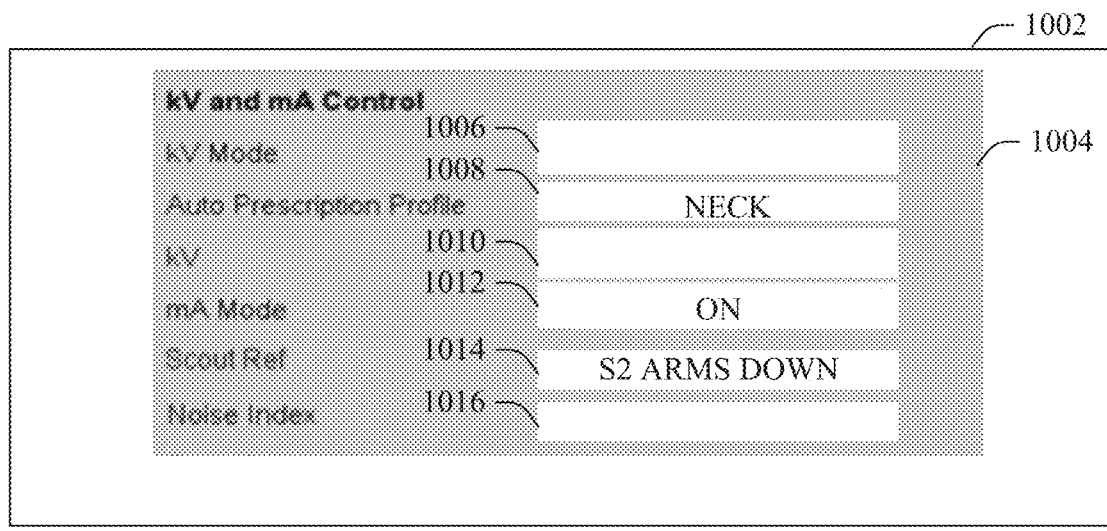
FIG. 10 schematically illustrates a non-limiting example of a protocol management window for a second group of the series with the scout reference image field populated, in accordance with an embodiment(s) herein.

In one instance, during scan planning, the user assigns the saved scout images to the groups of the series. In another instance, at scan time, the user assigns the scout images to the groups of the series. FIGS. 8, 9 and 10 illustrate an instance where a user identifies which saved scout image to use with which group of a series during scan planning and/or at scan time. In one instance, at scan time refers to assigning the scout images for a first time. In another instance, at scan time includes re-assigning scout images that were previously assigned during scan planning.

In FIG. 8, a UI 802 presents a kV and mA control window 804 for a first group of a series. The window 804 allows a user to set parameters such as kV Mode, Auto Prescription Profile, kV, mA Mode, Scout Ref, and Noise Index, respectively, via fields 806, 808, 810, 812, 814 and 816. For explanatory purpose, only the fields (808, 812 and 814) related to X-ray source current modulation and the scout image utilized therefore are discussed.

The Auto Prescription Profile field 808 indicates this group is for a chest scan and the mA Mode field 812 is set to "on" indicating X-ray source current modulation will be used. A window 818 presents two options for the Scout Ref field 814, scout 1 (S1) Arms Up 820 and scout 2 (S2) Arms Down 822. In general, the available files can be presented in a drop-down menu, a pop-up menu, a list box, a directory tree structure, and/or otherwise. FIG. 9 shows the window 804 with S1 Arms Up selected for the Scout Ref field 814.

In FIG. 10, a UI 1002 presents a kV and mA control window 1004 for a second group of the series. The window 1004 allows a user to set parameters such as kV mode, Auto Prescription Profile, kV, mA Mode, Scout Ref, and Noise Index, respectively, via fields 1006, 1008, 1010, 1012, 1014 and 1016. Again, for explanatory purposes, only the fields (1008, 1012 and 1014) related to X-ray source current modulation and the scout image utilized therefore are discussed.

In one instance, the Scout Ref field 1014 is automatically populated with S2 Arms Down because S1 Arms Up was selected in the kV and mA control window 804 for the first group of the series and there are only two options, one for each of the groups. In another instance, the user selects the file similar to selecting the file in the kV and mA control window 804. In one instance, both file names are presented, and user selects S2 Arms Down 822. In another instance, S1 Arms Up is removed from the options because it has already been assigned to the first group of the series.

During the scan session, the scout image selected in the kV and mA control window 804 is utilized for X-ray source current modulation for the first group of the series and the scout image selected in the kV and mA control window 1004 is utilized for X-ray source current modulation for the second group of the series. Video and/or an image(s) from the camera 150 can be utilized at scan time to confirm the position of the arms of the subject for each of the two groups of the series before each group is performed. In one instance, the user at the operator console views the video and/or an image(s) to confirm the position. In another instance, AI trained to evaluate video and/or an image(s) and classify anatomy such as the arms is utilized to facilitate confirming the position. In another instance, the video and/or an image(s) is analyzed by an algorithm configured to contour the body and/or anatomical tissue with contour lines, such as drawing a contour line around the arms, to facilitate confirming the position.

Figure 11:
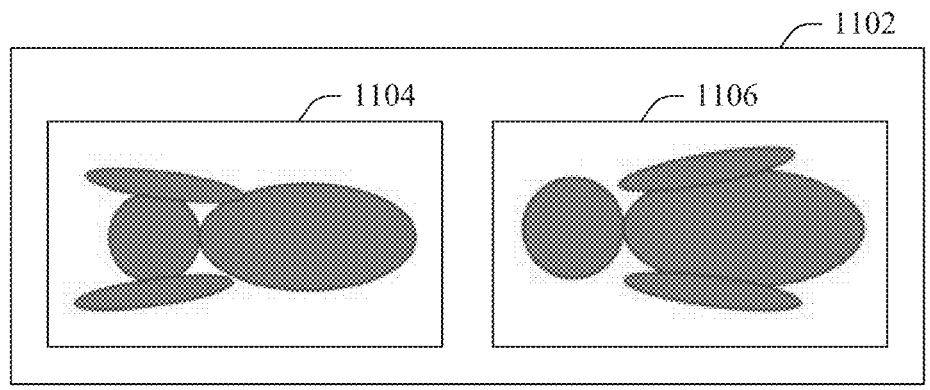
FIG. 11 schematically illustrates a non-limiting example of a graphical approach for designated scout images to groups, in accordance with an embodiment(s) herein.

FIG. 11 schematically illustrates another approach that can be used alternatively and/or in combination with the approach(s) described in connection with FIGS. 7-10.

In one instance, instead of naming a scout image based on user input, a window 1102 presents a graphic 1104 with arms of a subject up above their shoulders and a second graphic 1106 with the arms of the subject down by their side. The user selects one of the graphics 1104 or 1106, and the graphic maps or links the saved scout image to the group. In one instance, the other graphic automatically maps or links to the other scout image to the other group. In another instance, the user selects the other graphic from the window 1106, where the window 1102 shows both graphics 1104 or 1106 or shows just one graphic, the graphic that was not already selected.

The user can change the assignment of either or both of the scout images. Similar to FIGS. 8, 9 and 10, in one instance this approach is utilized during scan planning, in another instance this approach is utilized at scan time, and in another instance this approach is utilized during scan planning and at scan time. In one instance, the scout images were assigned during planning and the assignment is updated at scan time. In another instance, the scout images were not assigned during planning and the assignment is made at scan time.

As previously discussed in connection with FIGS. 4-6, the scout image 204, 216 or 306 and/or other scout images can be displayed in viewports during scan planning and/or scanning. It is to be appreciated that in one instance either or both of the scout images discussed in connection with FIGS. 7-11 can be displayed in viewports of FIGS. 4-6 during scan planning and/or scan time. In another instance, the scout image 216 or 306 with no arms can be utilized as one or both of the scout images in connection with FIGS. 7-11.

Figure 12:
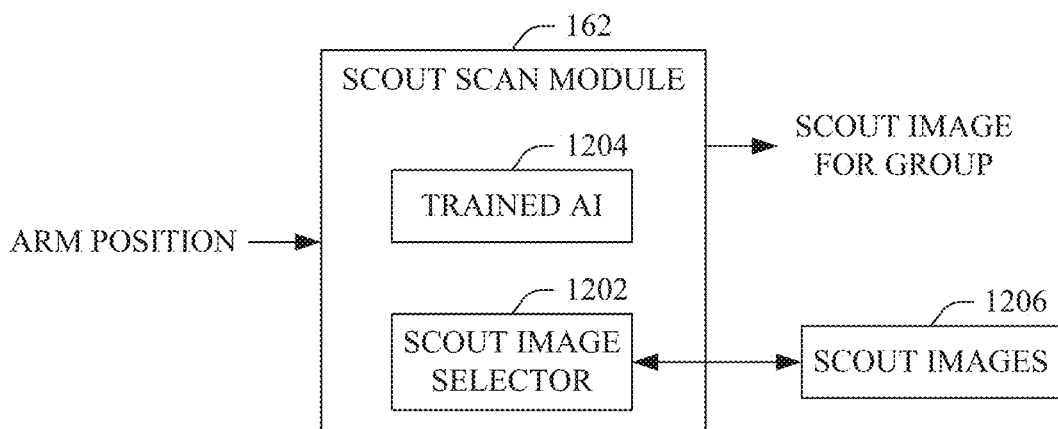
FIG. 12 schematically illustrates another non-limiting example of a scout scan module, in accordance with an embodiment(s) herein.

FIG. 12 schematically illustrates another non-limiting example of the scout scan module 162. The scout scan module 162 includes a scout image selector 1202 in communication with a bank of scout images 1206. The scout scan module 162 receives a current arm position of the current group and the scout image selector 1202 identifies a scout image from the bank of scout images 1206 with arms that match the current arm position. The scout scan module 162 outputs the scout image or a link thereto for the reference image for X-ray source current modulation for the group of the series.

In one instance, the user enters the current arm position. The user can determine the arm position by looking at the subject and/or video and/or an image(s) of the subject from the camera 150. In another instance, the group identifies the arm position. For example, if the user is about to start a chest scan, this indicates the arms will be up for the scan. In another instance, AI trained to analyze video and/or an image(s) of a subject and classify anatomical tissue, such as appendages like the arms, etc., identifies whether the arms are currently up or down. In another instance, an algorithm is utilized to contour body and/or anatomical tissue of the video and/or an image(s) with contour lines, such as contour line for the arms. The user can confirm or change the input arm position.

In one instance, the scout image selector 1202 identifies the scout image based on a Digital Imaging and Communications in Medicine (DICOM) field of the scout scans, e.g., a subject arm position field. In another instance, the AI trained to analyze video and/or an image(s) of a subject and classify anatomical tissue, determines whether the arms are up or down in the scout images. In another instance, the DICOM subject arm position field indicates that a scout image has no arms. In another instance, the trained AI indicates that a scout image has no arms.

Figure 13:
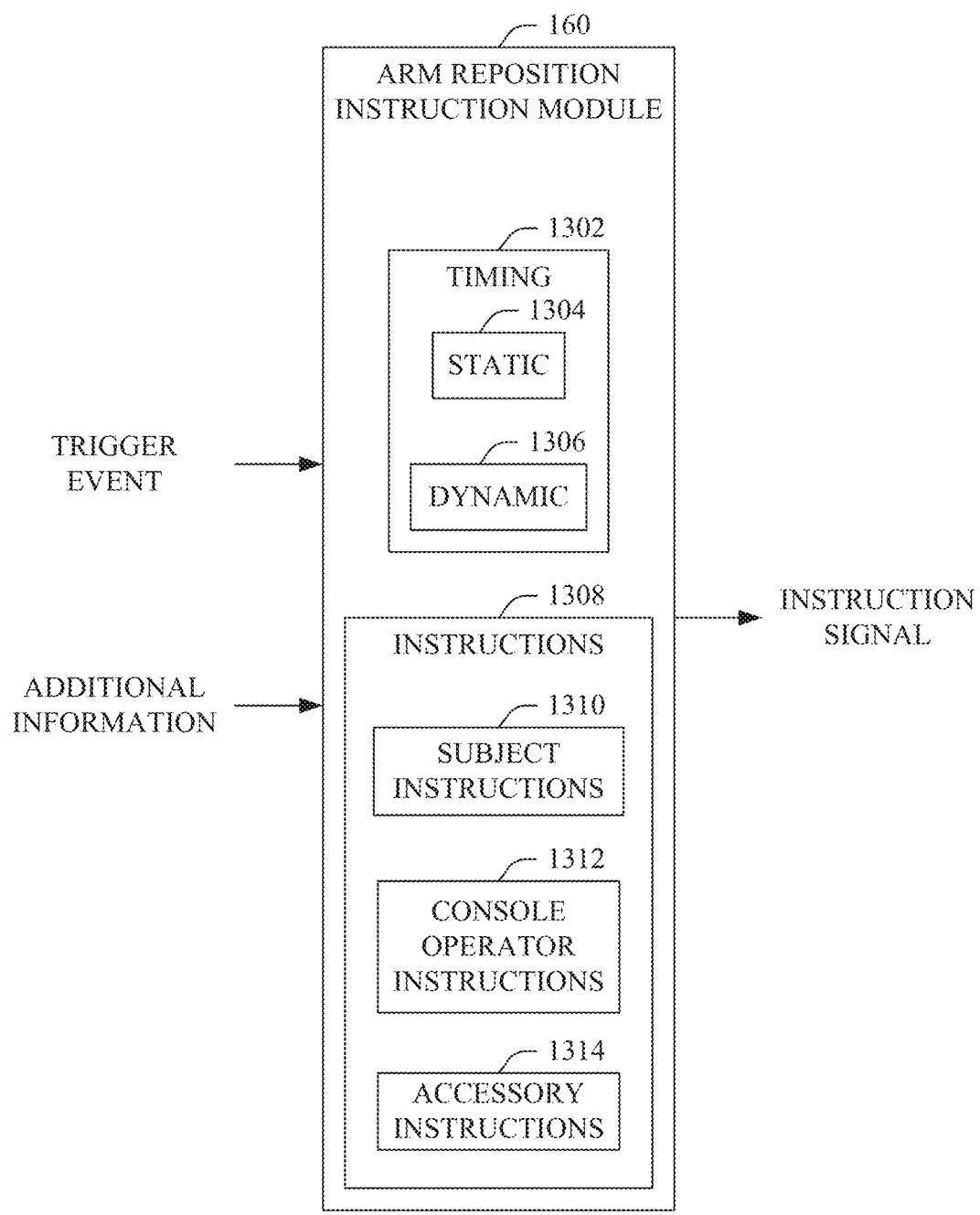
FIG. 13 schematically illustrates a non-limiting example of the arm reposition instruction module, in accordance with an embodiment(s) herein.

FIG. 13 illustrates a non-limiting example of the arm reposition instruction module 160. The arm reposition instruction module 160 includes a timing module 1302 with static instructions 1304 and dynamic instructions 1306 and an instructions module 1308 with subject instructions 1310, console operator instructions 1312, and accessory instructions 1314 (where the system 102 includes and/or utilizes an arm position accessory device). The arm reposition instruction module 160, based the position of the arms for the next group, provides an instruction timing signal or instructions for moving the arms to the correct position for the group.

The arm reposition instruction module 160 receives a trigger event as input. In one instance, a trigger event is a signal indicating the first group is finished. The signal can be from the system 102, the console operator, evaluation of video and/or an image(s) from the camera 150, etc. In another instance, the trigger event is a signal indicating an anatomical or physiological event. For example, the trigger event can indicate peak uptake of an image contrast agent has been detected. Depending on the trigger event, the timing module 1302 selects a static or dynamic rule from the static instructions 1304 and the dynamic instructions 1306.

An example of a rule for the static instructions 1304 includes providing instructions after a predetermined amount of time or delay after completion of the first group, e.g., two seconds after the first group. Where arm movement is not completed within the predetermined amount of time, a predetermined amount of time can be added to the predetermined amount of time, e.g., add five more seconds. An example of a rule for the dynamic instructions 1306 includes provide five seconds after detection of peak contrast agent uptake. Optionally, additional information can be utilized to determine the rule to implement. Examples of such additional information include an age of the subject, a physical state and/or mental state of the subject, whether the subject, the console operator and/or the arm positioning device accessory will reposition the arms.

The instructions 1308 include a set of available instructions, including audio, tactile, and/or visual instructions for repositioning the arms. In one instance, the subject repositions their arms by themselves. In another instance, the user of the operator console assists the subject with repositioning their arms. In another instance, an arm positioning device accessory is utilized to assist the subject with repositioning their arms. In another instance, a combination of subject and user assisted approaches, subject and arm positioning device accessory approaches, or subject, user assisted, and arm positioning device accessory approaches is utilized to assist the subject with repositioning their arms.

Examples of audio instructions include automated human or machine arm position verbal instructions, tones, a combination thereof, and/or other audio. The audio instructions are provided through speakers or the like in the scan room and/or to the console operator. Examples of tactile instructions include a vibrating device such as a watch, pendent, a combination thereof, and/or other tactile instructions. The tactile instructions provide tactile feedback in the scan room and/or to the console operator. Examples of visual instructions include a projected image, a light, a light pattern, a combination thereof, and/or other visual instructions. The visual instructions are provided on or near the system 102 and/or console operator, e.g., on the ceiling, on the system 102, on a display monitor of or near the system 102 and within a line of sight of the subject and/or operator console.

After the timing delay, the arm reposition instruction module 160 outputs an instruction signal. In one instance, the instruction signal causes the subject instructions 1310 to be sent to the subject. In one instance, the instruction signal causes the console operator instructions 1312 to be sent to the console operator. In one instance, the instruction signal causes the arm positioning device accessory instructions 1314 to be sent to the arm positioning device accessory. In another instance, instructions are provided to at least two of the subjects, user of the operator console and the arm positioning device accessory.

Figure 14:
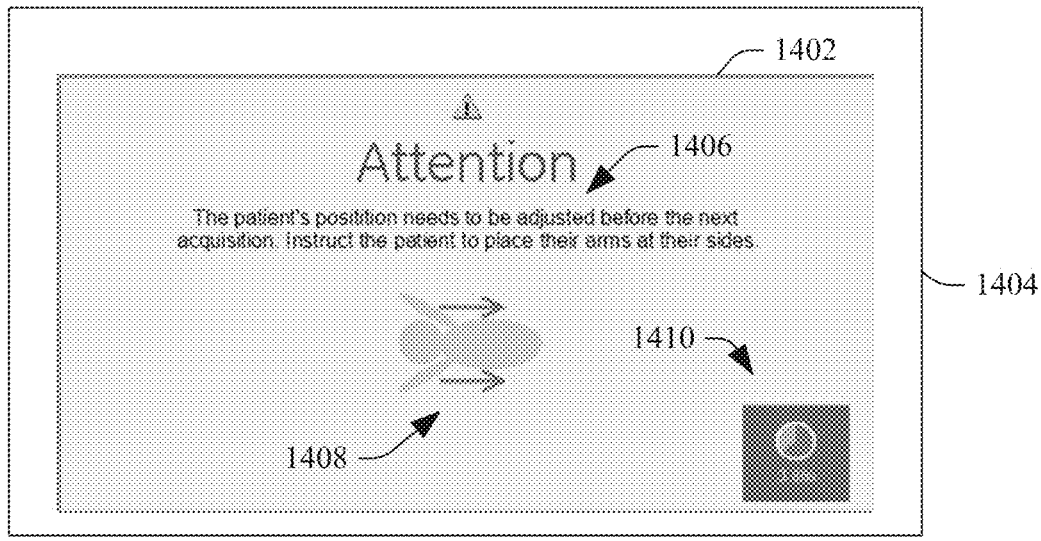
FIG. 14 illustrates a non-limiting example of a visual instruction, in accordance with an embodiment(s) herein.

FIG. 14 illustrates a non-limiting example of a visual instruction 1402 of the console operator instructions 1312. The visual instruction 1402 is displayed in a UI 1404 and includes a text based instruction 1406 and a graphical instruction 1408 and a timer 1410 counting down the arm reposition delay time determined by the instruction timing module 1302. In another instance, at least one of the text based instruction 1406, the graphical instruction 1408 or the timer 1410 is omitted from the visual instruction 1402. In another instance, the visual instruction 1402 and/or other visual instruction displays one color or pattern to indicate the subject should remain in a current position and another color or pattern to indicate the subject should transition to the new position.

Figure 15:
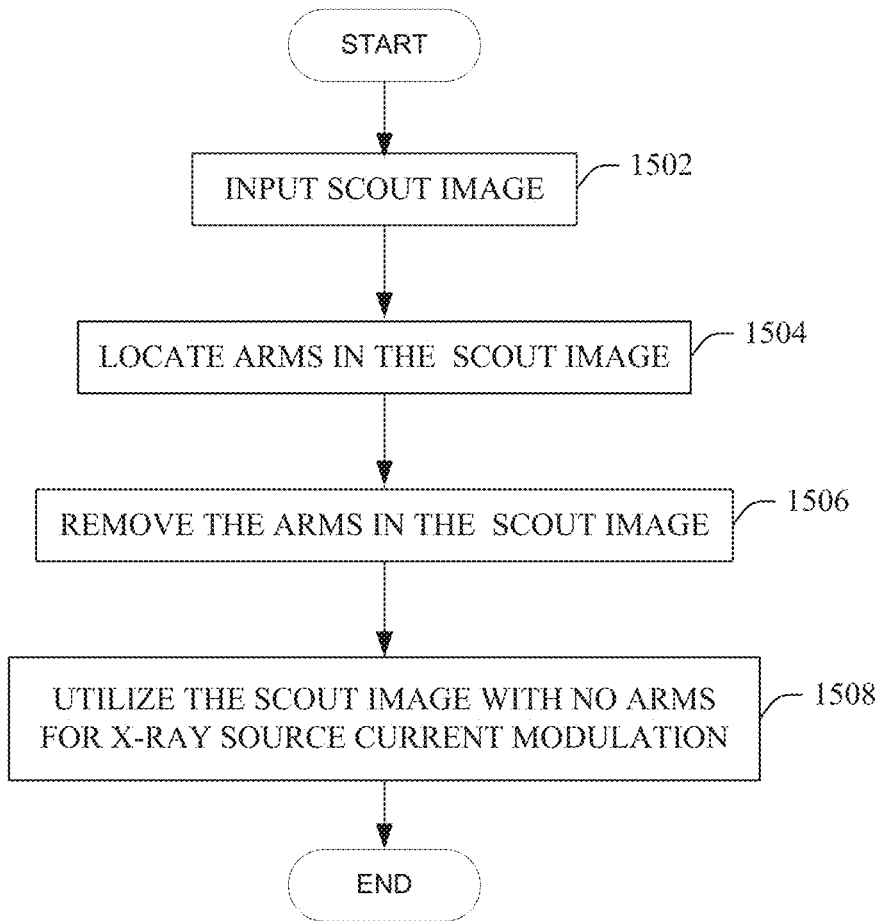
FIG. 15 illustrates a non-limiting example of a flow chart for a computer-implemented method, in accordance with an embodiment(s) herein.

FIG. 15 illustrates a non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included. At 1502, an input scout image in which arms of the subject are either up above their shoulders or down at their side is obtained, as described herein and/or otherwise. At 1504, the arms of the subject are identified in the scout image, as described herein and/or otherwise. At 1506, the identified arms of the subject are removed from the scout image thereby generating a scout image with no arms, as described herein and/or otherwise. At 1508, the scout image with no arms is assigned as the reference image for X-ray tube source modulation for all groups of a series, including a group where the arms of the subject are up and a group where the arms of the subject are down, as described herein and/or otherwise.

Figure 16:
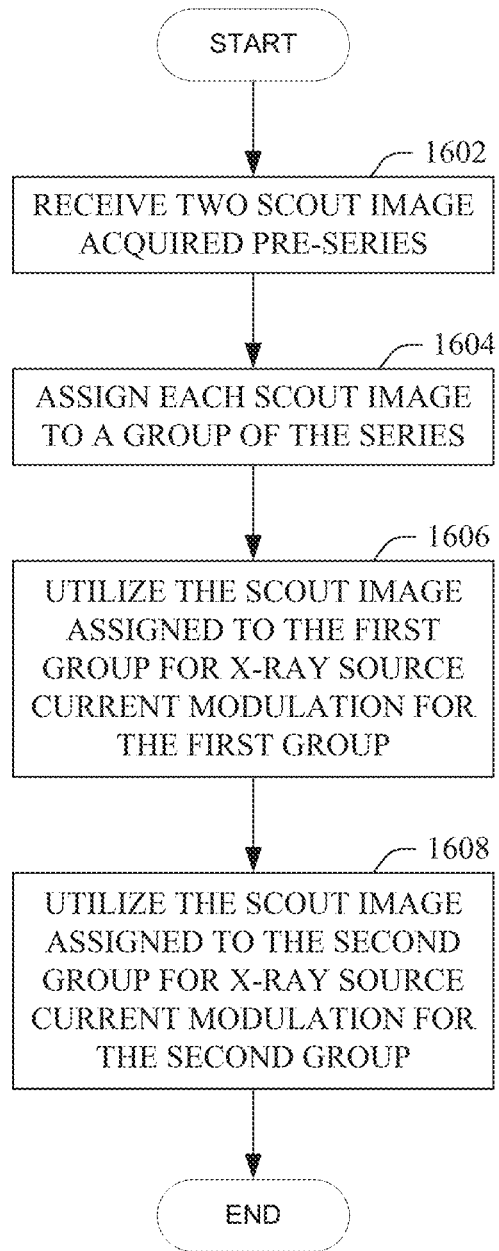
FIG. 16 illustrates another non-limiting example of a flow chart for a computer-implemented method, in accordance with an embodiment(s) herein.

FIG. 16 illustrates another non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included. At 1602, two scout images, one with arms of the subject up and one with the arms of the subject down, both acquired prior to a series, are obtained, as described herein and/or otherwise. At 1604, the scout with the arms up is assigned to the group of the series requiring the arms of the subject to be up and the scout with the arms down is assigned to the group of the series requiring the arms of the subject down. At 1606, during scanning of the first group, the scout image assigned thereto is utilized as the reference image for X-ray tube source modulation, as described herein and/or otherwise. At 1608, during scanning of the second group, the scout image assigned thereto is utilized as the reference image for X-ray tube source modulation, as described herein and/or otherwise.

Figure 17:
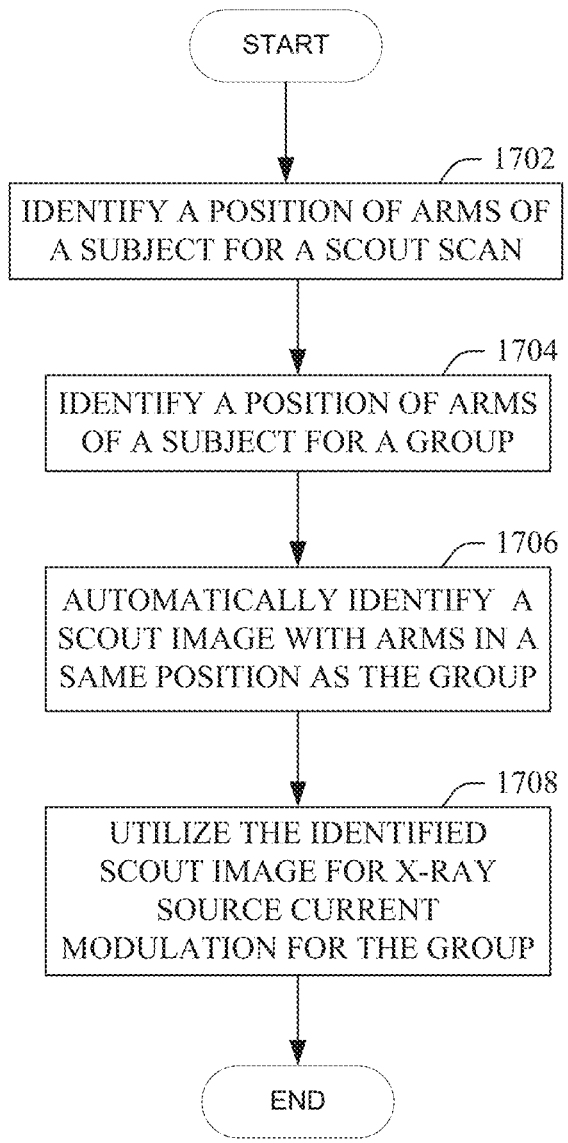
FIG. 17 illustrates another non-limiting example of a flow chart for a computer-implemented method, in accordance with an embodiment(s) herein.

FIG. 17 illustrates another non-limiting example of a flow chart for a computer-implemented method. It is to be appreciated that the ordering of the acts in the method is not limiting. As such, other orderings are contemplated herein. In addition, one or more acts may be omitted, and/or one or more additional acts may be included. At 1702, identify a position of arms of a subject for a scout scan, as described herein and/or otherwise. At 1704, identify a position of arms of a subject for a group, as described herein and/or otherwise. At 1706, automatically identify a scout image with arms in a same position as the arms for the group, as described herein and/or otherwise. At 1708, during scanning, automatically utilize the identified scout image for X-ray source current modulation for the group, as described herein and/or otherwise.

The above may be implemented by way of computer readable instructions, encoded or embedded on computer readable storage medium (which excludes transitory medium), which, when executed by a computer processor(s) (e.g., CPU, microprocessor, etc.), cause the processor(s) to carry out acts described herein. Additionally, or alternatively, at least one of the computer readable instructions is carried by a signal, carrier wave or other transitory medium, which is not computer readable storage medium.

As used herein, an element or step recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A computed tomography imaging system, comprising:
   a rotating frame configured to rotate about a rotational axis;
   an X-ray source disposed on the rotating frame and configured to emit X-ray radiation that traverses an examination region;
   an X-ray controller configured to control the X-ray source;
   a subject/object support configured to support a subject or object in the examination region;
   a console, including:
      a computer readable medium configured to store instructions; and
      a processor configured to execute the instructions, wherein the instructions cause the processor to:
         obtain a first scout image with arms of a subject up above shoulders of the subject;
         obtain a second scout image with arms of the subject down by sides of the subject,
         designate the first scout image as a reference image for X-ray source current modulation for a first group of a scan series where the arms of the subject are up above the shoulders of the subject;
         designate the second scout image as a reference image for X-ray source current modulation for a second group of the scan series where the arms of the subject are down by the sides of the subject; and
         command the X-ray controller to utilize the first scout image as the reference image for X-ray source current modulation for the first group of the scan series and the second scout image as the reference image for X-ray source current modulation for the second group of the scan series.

2. The computed tomography imaging system of claim 1, wherein the first scout image and the second scout image are acquired prior to planning the scan series.

3. The computed tomography imaging system of claim 1, wherein the instructions further cause the processor to:

save the designations into a scan plan for the series through parameter settings.

4. The computed tomography imaging system of claim 1, wherein the instructions further cause the processor to:
select or update the designations at scan time through parameter settings.

5. The computed tomography imaging system of claim 1, wherein the instructions further cause the processor to:
select or update the designations at scan time through a graphical selection.

6. The computed tomography imaging system of claim 1, further comprising:
a display monitor, wherein the instructions further cause the processor to:
visually present a user interface with at least two viewports during scanning on the display monitor; wherein the processor displays an image reconstructed during scanning in a first of the at least two viewports, displays the first scout image in a second of the at least two viewports with indicia indicating a location of the image reconstructed along the first scout image for the first group, and displays the second scout image in the second of the at least two viewports with indicia indicating a location of the image reconstructed along the second scout image for the second group.

7. The computed tomography imaging system of claim 1, further comprising:
a camera, wherein the instructions further cause the processor to:
determine a current position of the arms of the subject based on a signal from the camera.

8. The computed tomography imaging system of claim 1, further comprising:
a camera, wherein the instructions further cause the processor to:
confirm a position of the arms of the subject prior to each group of the at least two groups based on a signal from the camera.

9. The computed tomography imaging system of claim 1, wherein one of the first scout image and the second scout image includes a processed scout image with no arms.

10. A computer-implemented method, comprising:
obtaining a first scout image for a first group of a scan series, wherein the first scout image includes arms of a subject up above shoulders of the subject;
obtaining a second scout image for a second group of the scan series, wherein the second scout image includes arms down by sides of the subject,
wherein the first scout image and the second scout image are acquired prior to planning the scan series, the first group includes the arms of the subject up above the shoulders of the subject, and the second group includes the arms of the subject down by the sides of the subject;
designating the first scout image as a reference image for X-ray source current modulation for the first group; and
designating the second scout image as a reference image for X-ray source current modulation for the second group.

11. The computer-implemented method of claim 10, further comprising:
operating an imaging system to utilize the first scout image as the reference image for X-ray source current modulation for the first group and the second scout image as the reference image for X-ray source current modulation for the second group.

12. The computer-implemented method of claim 10, further comprising:
saving the first scout image with a first file name that indicates arm position in the first scout image; and
saving the second scout image with a second file name that indicates arm position in the second scout image.

13. The computer-implemented method of claim 10, further comprising:
displaying a window that includes a first field designating a scout scan for the first group;
receiving an input indicative of a user selection of a first file name or a second file name for the first field;
populating the first field based on the input; and
automatically populating a second field of a second window designating a scout scan for the second group with an unselected one of the first file name or the second file name.

14. The computer-implemented method of claim 10, further comprising:
displaying a first visual representation indicating subject arms up, wherein the visual representation is a graphic with the arms of the subject up above shoulders of the subject or the first scout image with the arms of the subject up above shoulders of the subject;
displaying a second visual representation indicating subject arms down, wherein the visual representation is a graphic with the arms of the subject down by sides of the subject or the second scout image with the arms of the subject down by the sides of the subject;
receiving an input indicative of a user selection of the first or second visual representation for the first group or the second group;
linking the first scout image to the first group in response to the input indicating a user selection of the visual representation and automatically linking the second scout image to the second group based on the linking of the first scout image, or
linking the second scout image to the first group in response to the input indicating a user selection of the second visual representation and automatically linking the first scout image to the second group based on the linking of the second scout image.

15. A non-transitory computer readable medium encoded with computer executable instructions, which when executed by a processor, cause the processor to: obtain a first scout image for a first group of a scan series, wherein the first scout image includes arms of a subject up above shoulders of the subject; obtain one or more additional scout image for one or more additional group of the scan series, wherein the one or more additional scout image includes arms down by sides of the subject, wherein the first scout image and the one or more additional scout image are acquired prior to planning the scan series, the first group includes the arms of the subject up above the shoulders of the subject, and the one or more additional group includes the arms of the subject down by the sides of the subject; designate the first scout image as a reference image for X-ray source current modulation for the first group; and designate the one or more additional scout image as a reference image for X-ray source current modulation for the one or more additional group.

16. The computer readable medium of claim 15, where the instructions further cause the processor:
control an imaging system to utilize the first scout image as the reference image for X-ray source current modulation for the first group and the one or more additional scout image as the reference image for X-ray source current modulation for the one or more additional group.

17. The computer readable medium of claim 15, where the instructions further cause the processor:
designate the first scout image and the one or more additional scout images during planning the series.

18. The computer readable medium of claim 15, where the instructions further cause the processor:
designate the first scout image and the one or more additional scout images at scan time.

19. The computer readable medium of claim 15, where the instructions further cause the processor:
display the first scout image or the one or more additional scout image with indicia indicating a location of a next reconstructed image in a viewport.

20. The computer readable medium of claim 15, where the instructions further cause the processor:
display both the first scout image and the one or more additional scout image with indicia indicating a location of a next reconstructed image in a viewport.

* * * * *